United States Patent [19]

Eden et al.

[11] Patent Number: 4,755,397
[45] Date of Patent: Jul. 5, 1988

[54] STARCH BASED PARTICULATE ENCAPSULATION PROCESS

[75] Inventors: James Eden, East Millstone; Ralph Trksak, Manville, both of N.J.; Robert Williams, Homosassa, Fla.

[73] Assignee: National Starch and Chemical Corporation, Bridgewater, N.J.

[21] Appl. No.: 946,266

[22] Filed: Dec. 24, 1986

[51] Int. Cl.$^4$ .......................... A61K 9/62; B01J 13/02; C09C 1/24; C09C 3/10
[52] U.S. Cl. ............................... 427/213.3; 71/64.11; 71/DIG. 1; 106/501; 264/4.3; 264/4.4; 424/488; 424/499; 426/103; 426/650; 426/651; 427/213.33; 428/402.2; 428/402.24; 514/963
[58] Field of Search ...................... 264/4.4; 427/213.3; 428/402.2, 402.24; 424/488, 499; 426/103

[56] References Cited

U.S. PATENT DOCUMENTS

| | | | |
|---|---|---|---|
| 2,369,847 | 12/1941 | Olsen et al. | 99/140 |
| 2,809,895 | 7/1955 | Swisher | 99/140 |
| 2,902,336 | 9/1959 | Hiemstra et al. | 18/54 |
| 3,030,667 | 4/1962 | Kunz | 18/57 |
| 3,041,180 | 6/1962 | Swisher | 99/140 |
| 3,116,351 | 12/1963 | Wohlrabe et al. | 264/186 |
| 3,336,429 | 8/1967 | Carevic | 264/186 |
| 3,499,962 | 8/1967 | Wurzburg et al. | 424/35 |
| 3,514,298 | 3/1968 | Nozmick et al. | 99/123 |
| 3,786,123 | 1/1971 | Katzen | 264/53 |
| 3,922,354 | 11/1975 | Galluzzi et al. | 426/96 |
| 3,971,852 | 7/1976 | Bremmer et al. | 426/103 |
| 4,139,699 | 2/1979 | Hernandez et al. | 536/109 |
| 4,230,687 | 10/1980 | Sair et al. | 424/22 |
| 4,242,364 | 12/1980 | Buddemeyer et al. | 426/613 X |
| 4,243,480 | 1/1981 | Hernandez et al. | 162/141 |
| 4,276,312 | 6/1981 | Merritt | 426/96 |
| 4,277,364 | 7/1981 | Shasha et al. | 252/316 |
| 4,331,689 | 5/1982 | Shemwell | 426/103 X |
| 4,344,857 | 8/1982 | Shasha et al. | 252/316 |
| 4,382,813 | 5/1983 | Shasha | 71/88 |
| 4,439,488 | 3/1984 | Trimmell et al. | 428/402.24 |
| 4,657,582 | 4/1987 | Huber | 71/121 |

FOREIGN PATENT DOCUMENTS 0145846  8/1984  European Pat. Off. .
1072795  6/1967  United Kingdom .

Primary Examiner—Richard D. Lovering
Attorney, Agent, or Firm—Ellen T. Dec; Edwin M. Szala

[57] ABSTRACT

A wide range of materials may be encapsulated in a starch matrix by combining the material with a high temperature-stabilized pressurized dispersion of starch in the presence of salt. The temperature-stabilized starch dispersion acts as a protective colloid; upon subsequent rapid reduction of the pressure, the mixture cools and the starch polymer chains collapse upon themselves, encapsulating the core material in particulate form.

9 Claims, No Drawings

STARCH BASED PARTICULATE ENCAPSULATION PROCESS

BACKGROUND OF THE INVENTION

The present invention is directed to a method for the encapsulation of materials in a matrix composed of unmodified or modified starch under conditions that reduce or eliminate the decomposition and/or loss of the material being encapsulated.

Many methods have been employed in the prior art to encapsulate a variety of materials. In general, the specific method employed as well as the encapsulating agent utilized has been dependent on the type of material being encapsulated. Thus the volatile or nonvolatile nature of the material as well as its water or oil solubility have been the prinical factors controlling the method of encapsulation and the encapsulating materials chosen.

SUMMARY OF THE INVENTION

We have now found a method for encapsulating a wide variety of materials using starch as the encapsulating agent.

In accordance with the present invention, the materials to be encapsulated are combined with a high temperature-stabilized dispersion of starch in a saturated salt solution. The temperature-stabilized starch dispersion acts as a protective colloid, encasing the material to be encapsulated. Upon subsequent rapid cooling of this mixture the starch polymer chains collapse upon themselves, forming a highly crystalline particulate-form matrix encapsulating the core material. In the resultant precipitate, the material being encapsulated is evenly distributed throughout the starch matrix. However, the starch in the resultant encapsulated products is highly retrograded, thus forming a water insensitive product.

The encapsulation process of the present invention comprises the following steps:

(1) slurrying the starch and the material to be encapsulated in water in a saturated aqueous solution of salt;
(2) thoroughly dispersing the starch in the presence of the salt by injecting steam at a pressure of at least 110 psi into the slurry to raise its temperature to 120° to 180° C. at a pressure of 55–120 psi or above;
(3) instantly reducing the pressure developed during step 2 to atmospheric pressure so as to reduce the temperature to 112° C. or less; and
(4) recovering the precipitated-retrograded starch particles which encapsulate the added material. If desired, the salt used in the encapsulation process may be washed from the dried starch matrix.

DETAILED DESCRIPTION OF THE PREFERRED EMBODIMENTS

A wide range of materials may be encapsulated using the process disclosed herein. The only limitations with respect to the core material to be encapsulated are that it be insoluble in the salt solution at the exit temperature from the reactor; that it have a boiling point greater than the exit temperature; and that it not react with water or the salt under the processing conditions. Representative materials include flavors and seasonings including flavoring oils; pigments; metallic powders; latices; oils; plasticizers; herbicides; insecticides; fungicides; nematicides; bacteriocides; rodenticides; molluscicides; acaricides; larvacides; fumigants; animal repellants; insect repellants; plant growth regulators; fertilizers; pheromones; odor producing compositions; enzymes; drugs, vitamins; fabric softeners; temperature indicators; catalysts; adhesives; pressure sensitive color formers; electrostatographic toners; pressure rupturable lubricants; antifoulants; phase change materials; fire extinguishers; corrosion inhibitors; defoamers; sizing agents; thickeners; unsaturated fats and acidulants. Depending upon the type of core material employed, from as little as 0.1% to as much as 80% by weight core material (solids based on starch plus salt plus core material) may be encapsulated in the starch matrix.

The process of the invention is not limited to any specific starch encapsulating materials. Corn starch, rice starch, potato starch, tapioca starch, wheat starch, amylose or amylopectin fractions may be employed. The starch base may be used in modified or unmodified form. The choice of the starch to be used is dependent in large part on the end use of the encapsulated material particularly the mechanism and desired rate of release, if any, of the material from the encapsulating matrix.

In addition to the use of starch as the encapsulating material, water soluble hydrocolloids such as polyvinyl alcohol, carboxymethylcellulose, hydroxyethylcellulose, polyacrylic acid and polyvinyl pyrrolididone may replace up to 50% of the starch component.

The salts used herein include ammonium sulfate, ammonium monobasic or di-basic phosphate, magnesium sulfate, sodium sulfate and mixtures thereof. Although there is no requirement regarding the selection of any of the above components used in the process, once determined, the ratios of the components are interrelated. Thus, the ratio of salt, starch and water in the slurry are dependent upon the starch selected. Those starches containing high levels of amylose require less salt to effect rapid precipitation while amylopectin based starches or dextrins may require saturated or supersaturated levels at the exit temperature. Similarly, the level of amylose in the starch effects the choice and concentration of the salt required for efficient precipitation, with the higher amylose containing starches capable of forming an encapsulated particle with any of the salts mentioned above while the starches with lower levels of amylose require higher levels of the preferred salts such as ammonium sulfate and magnesium sulate for efficient precipitation rates. The amount of starch usually varies from about 5 to 40% solids in the aqueous slurry. For efficient precipitation, saturated salt solutions are generally employed and since the salt may be recovered and recycled, amounts in excess of saturation may also be used to facilitate processing. In all cases, the levels of the components should be such that the starch/salt/water ratio does cause retrogradation prior to precipitation.

In general, the process of the invention involves the following steps, all of which may be conducted in a continuous manner.

First, a slurry of starch (and any hydrocolloid present), the material to be encapsulated and a salt is formed. If ammonium sulfate or ammonium phosphate is used, it may be necessary to add an acidic material to lower the pH to 8 or below. No pH adjustment is needed if magnesium sulfate is the salt used as it is effective under both acidic and basic conditions. As noted above, starch solids content in the slurry will vary between about 5 and 40% by weight of the slurry.

The temperature of the slurry is then raised via steam injection to a temperature high enough to disperse the starch in the salt solution. This temperature is generally in the range of 120° to 180° C. As the starch/core matrix exits the cooker, the temperature of the matrix is rapidly lowered to less than 112° C., as by flashing off any residual steam or by passing the mixture into a chilled salt bath. Through the process of retrogradation or association (hydrogen bonding) a mass of particles, either in slurry form or with no visible water is formed. This mass of particles can then be dried by conventional methods to produce the starch matrix containing the encapsulated material uniformly dispersed therethrough.

The particles may then be removed from the salt solution by filtration, centrifugation, or other means, optionally washed and dried. High amylose containing starch particles dried without washing retain their as-precipitated dimensions and do not fuse. Lower amylose containing starches fuse on drying to some degree and require agitation during drying or grinding after drying to produce a uniform particle size.

If desired, the material to be encapsulated may be added to the already cooked starch just prior to exiting the cooker and entering the flash chamber, however no practical advantage is achieved thereby except in the case of certain heat sensitive materials which would otherwise volatilize or degrade under extended exposure to the cooking step but which would not degrade under brief exposure to the high temperatures.

The release characteristics, i.e., the ability of the encapsulated core material to be released from the starch matrix, can be varied by the practitioner to permit farily rapid release by using an undried, low-amylose, high moisture particulate mass to a very slow release rate using a dried, high-amylose starch particulate mass. Similarly, the temperature at which the release will be effected can be varied from as low as about room temperature using a dextrin based starch to over 90° C. using a high amylose starch base.

Additionally, particle size may be controlled by varying shear at the point of precipitation and/or by varying starch or salt solids. In this regard, increasing the shear will reduce the particle size while use of higher solids levels will generally increase the particle size.

Since the resultant dried matrix is resistant to acid and alkali, it is possible to further react the matrix with crosslinking agents or cationic or anionic groups. It can be oxidized or chemically modified in other ways without affecting the core material encapsulated therein.

In the following examples, which are for illustrative purposes only, all parts are by weight and all temperatures in degrees Celsius unless otherwise noted.

EXAMPLE 1

Encapsulation of Ferric Hydroxide

Ferric chloride was dissolved in acidified water, dilute sodium hydroxide was added, while stirring, to precipitate fine ferric hydroxide. Ammonium sulfate, water and high amylose (70%) corn starch were added to the ferric hydroxide slurry to give a slurry of the following composition:

| | | |
|---|---|---|
| Starch | 410 grams | 19.9% |
| Ammonium sulfate | 610 grams | 29.6% |
| Ferric Hydroxide | 41 grams | 2.0% |
| Water | 1000 grams | 48.5% |

This slurry was processed through a jet cooker (Model C-1, National Starch & Chemical Corp.) at 150° C. At this temperature the high amylose starch cooked, despite the presence of a high level of an inhibiting salt, and formed a uniform dispersion. A ball valve had been attached to the outlet of the jet cooker. This valve was adjusted so that a pressure drop from maximum cooking temperature and pressure to atmospheric pressure occured as the starch cook passed through the valve. Upstream the pressure was 90 psig; downstream the pressure was essentially 0 psig.

As the starch passed through the valve and the pressure was reduced to atmospheric, its temperature dropped to 104° C, the boiling point of the salt solution at atmospheric pressure. At this temperature, the starch precipitated essentially instantaneously entrapping the ferric hydroxide. The product collected at the cooker outlet was a slurry of tan particles 5 to 7 microns in diameter. The slurry, by volume, was one third salt solution and two thirds precipitated particles. This product was washed free of salt and dried.

To test the efficiency of the encapsulation method, a portion of the resulting free flowing powder was suspended in water adjusted to pH 3.0 with hydrochloric acid. A control suspension was made with uncooked high amylose corn starch and ferric hydroxide at the same concentrations in pH 3.0 water. The pH was readjusted to 3.0 daily, if necessary. The encapsulated iron leached at one fourteenth the rate, 0.015 ppm/day, of the unencapsulated control, 0.22 ppm/day, showing the protective effect of the encapsulating starch.

EXAMPLE 2 pH Range of Process

Unlike some previous encapsulation processes, the present invention can be used to encapsulate core materials at a wide range of pHs ranging from less than 3 to at least 12 with only minor changes in process conditions. While a wide range of pH may be used, the pH has an effect upon the choice of salt employed. Since the ammonium salts are unstable above a pH of about 8, use of magnesium sulfate at these alkaline conditions is dictated.

A slurry was made of the following dry weight percentages:

| | |
|---|---|
| High Amylose (70%) Corn Starch | 19.6% |
| Ammonium Sulfate | 39.4% |
| Water | 41.0% |

Four portions were taken and adjusted to pH 3, 4, 5, and 8 with hydrochloric acid or sodium hydroxide as required. These were then jet-cooked through a cooker at 150° C. as in Example 1. The following products were obtained:

| pH | Physical Description | Softening point/ aqueous slurry |
|---|---|---|
| 3 | Particles 15–30 microns | 70° C. |
| 4 | Mixture Particles 15 60 microns | 75° C. |
| 5 | 5 micron Particles fused into 50–200 microns | 80° C. |

| pH | Physical Description | Softening point/ aqueous slurry |
|---|---|---|
| 8 | 5 micron Particles fused into 100 microns | 75° C. |

While these products did not contain any core material, any of the types previously mentioned could have been added and encapsulated as in Example 1.

Encapsulations at higher pH levels were performed using slurries made of the following composition:

| High Amylose (70%) Corn Starch | 25 parts |
|---|---|
| Magnesium Sulfate | 35 parts |
| Water | 40 parts |

Portions were adjusted to pH 8, 9, 10 and 12 with sodium hydroxide and each slurry was jet cooked as described above.

The product of each cooked slurry was a suspension of firm retrograded starch particles in clear salt solution. Core material, if present in the slurry, would have been entrapped in the manner described above.

EXAMPLE 3

Encapsulation of a Water Insoluble Liquid: Peppermint Oil

A slurry was made of the following composition:

| High Amylose (70%) Corn Starch | 20 parts |
|---|---|
| Ammonium Sulfate | 40 parts |
| Water | 40 parts |

The following were mixed, to disperse the peppermint oil and added, with mixing, to the previous slurry:

| Peppermint Oil, Redistilled, A. M. Todd Co | 4 parts |
|---|---|
| Surfactants | .92 parts |

The resulting slurry/coarse emulsion was jet-cooked through a C-1 cooker as in Example 1. In this case, the cooker outlet hose emptied below the surface of a slurry of ammonium sulfate and ice in saturated amonium sulfate solution (−8° C.) to condense and trap any free peppermint oil vapors. The resulting product was coarse (<20 mesh) light tan powder in salt solution. The powder was recovered by filtration and dried.

The following extraction procedure was used to prepare the gas chromatography (GC) analysis samples: 2 g of air dry starch peppermint matrix was dissolved in 19 g dimethylsulfoxide (DMSO) in a sealed vial using gentle heat. The DMSO solution of starch was cooled and 10 g of methylene chloride (containing 0.1% chloroform for use as an internal GC standard) was added to precipitate the starch. Next, 2 g water was added to destabilize the DMSO/methylene chloride solution. On addition of water two phases separated, the lower was methylene chloride with peppermint oil the upper was DMSO and water. An aliquot of the lower phase was analyzed using a Hewlett Packard Model 5890 gas chromatograph to determine heptane concentration. A HP-1 capillary column 10 meters by 0.53 mm with methyl silicone gum stationary phase was used. Sample size was 1 microliter. Injector sample split was 98:2. Temperature programming was: 50 C., 2 min; 25 degrees per min rise to 300 C.; hold at 300 C., 5 min. Results of the analysis showed the dried product to contain 3.75 peppermint oil on dry starch.

EXAMPLE 4

As discussed previously, virtually any starch can be used in this process. This includes high amylose starch, very low amylose starch such as waxy maize, or starch of moderate amylose level such as corn starch. The starch used may also be modified. Acid fluidity starch, oxidized starch, starch reacted with anionic or cationic reagents or with both, all can be precipitated by the range of process conditions permitted by this process. The procedure of Example 1 was used to produce particles from a variety of starch bases as noted below.

| Starch | Salt | Water | Particle Size |
|---|---|---|---|
| Waxy Maize one part | $(NH_4)_2SO_4$ 4 parts | 4 parts | 20 microns |
| Corn 40WF one part | $(NH_4)_2SO_4$ 4 parts | 4 parts | 10–20 microns |

The above were collected in iced saturated ammonium sulfate solution, as in Example 3, to prevent agglomeration of the particles.

| Starch | Salt | Ferric Chloride | Water | Particle Size |
|---|---|---|---|---|
| Amphoteric Waxy Maize one part | $(NH_4)_2SO_4$ 4 parts | 0.1 part | 4 parts | approx. 20 microns |
| 75WF chlorinated corn one part | $(NH_4)_2SO_4$ 4 parts | 0.1 part | 4 parts | approx. 15 microns |

As before, the particles were collected in iced saturated ammonium sulfate solution. The products, reddish brown powders, were filtered from the clear salt solutions, washed free of salt with distilled water and analyzed for iron. Results, using the Hach FerroZine method (Hach Co. Water Analysis Handbook 1983 edition, p. 2-137), showed essentially 100% retention of the iron in the starch particles.

EXAMPLE 5

A portion of the starch used may be replaced with a hydrocolloid that is water dispersible at high temperature and precipitated by salt at lower temperatures. Useable polymers include: polyvinyl alcohol, Kelgin, carboxymethyl cellulose, sodium polyacrylic acid and by extension many other natural and synthetic polymers.

Slurries were made of the following compositions:

| High Amylose (70%) Corn Starch | 21.6 parts |
|---|---|
| Polymer | 2.16 parts |
| Ammonium Sulfate | 25 parts |
| Water | 41.25 parts |

Polymers used were: Elvanol (71-31) Polyvinyl Alcohol (Dupont), Natrosol 250HR Carboxymethyl Cellulose (Hercules), and Kelsan S Kelgin (Kelco).

These slurries are jet cooked at 150° C. as described above and the products collected. The resulting materials were suspensions of particles in salt solution.

Now that the preferred embodiments of the present invention have been described in detail, various modifications and improvements thereon will become readily apparent to those skilled in the art. Accordingly the spirit and scope of the invention are to be limited only by the appended claims and not by the foregoing specifications.

We claim:

1. A process for the encapsulation of materials in a particulate form starch matrix comprising the steps of:
   (1) slurrying the starch and the material to be encapsulated in a saturated aqueous solution of salt;
   (2) thoroughly dispersing the starch in the presence of the salt by injecting steam at a pressure of at least 110 psi into the slurry to raise its temperature to 120° to 180° C. at a pressure of 55-120 psi or above;
   (3) instantly reducing the pressure developed during step 2 to atmospheric pressure so as to reduce the temperature to 112° C. or less; and
   (4) recovering the precipitated encapsulated material.

2. The process of claim 1 wherein the material to be encapsulated is selected from the group consisting of flavoring oils; pigments; metallic powders; latices; oils; plasticizers; herbicides, insecticides; fungicides; nematocides; bacteriocides; rodenticides; molluscicides; acaricides; larvacides; fumigants; animal repellants; insect repellants; plant growth regulators; fertilizers; pheromones; odor producing compositions; catalysts; adhesives; pressure sensitive color formers; electrostatographic toners; pressure rupturable lubricants; antifoulants; phase change materials; fire extinguishers; corrosion inhibitors; defoamers; sizing agents; thickeners; unsaturated fats and acidulants.

3. The process of claim 1 wherein up to 50% of the starch is replaced by a water soluble hydrocolloid.

4. The process of claim 3 wherein the water soluble hydrocolloid is selected from the group consisting of polyvinyl alcohol, carboxymethylcellulose, hydroxyethylcellulose, polyacrylic acid and polyvinyl pyrrolididone.

5. The process of claim 1 wherein the starch employed contains more than 50% amylose.

6. The process of claim 1 wherein a salt selected from the group consisting of ammonium sulfate, ammonium monobasic or dibasic phosphate, magnesium sulfate, sodium sulfate and mixtures thereof is present in the starch slurry.

7. The process of claim 6 wherein the starch contains less than 50% amylose.

8. The process of claim 6 wherein the salt is ammonium sulfate or ammonium phosphate and the pH of the slurry is adjusted to a pH of 8 or below.

9. The process of claim 6 wherein the salt is magnesium sulfate.

* * * * *